(12) United States Patent
Onozawa et al.

(10) Patent No.: US 6,743,933 B2
(45) Date of Patent: Jun. 1, 2004

(54) PROCESS OF FORMING THIN FILM AND PRECURSOR FOR CHEMICAL VAPOR DEPOSITION

(75) Inventors: Kazuhisa Onozawa, Tokyo (JP); Atsuya Yoshinaka, Tokyo (JP); Naoki Yamada, Tokyo (JP); Atsushi Sakurai, Tokyo (JP)

(73) Assignee: Asahi Denka Co., Ltd., Tokyo (JP)

( * ) Notice: Subject to any disclaimer, the term of this patent is extended or adjusted under 35 U.S.C. 154(b) by 0 days.

(21) Appl. No.: 10/286,906

(22) Filed: Nov. 4, 2002

(65) Prior Publication Data

US 2003/0124251 A1 Jul. 3, 2003

(30) Foreign Application Priority Data

Nov. 15, 2001 (JP) .......................... 2001-350691

(51) Int. Cl.$^7$ .............................. C07F 7/28; C23C 16/18
(52) U.S. Cl. .................... 556/40; 556/54; 427/587; 427/593
(58) Field of Search ................ 556/40, 54; 427/587, 427/593

(56) References Cited

U.S. PATENT DOCUMENTS

| | | | | |
|---|---|---|---|---|
| 4,438,039 A | * | 3/1984 | Beers et al. ................... | 556/40 |
| 6,280,518 B1 | * | 8/2001 | Itsuki et al. ............ | 106/287.19 |
| 6,603,033 B2 | * | 8/2003 | Woo ............................. | 556/40 |

FOREIGN PATENT DOCUMENTS

| | | | |
|---|---|---|---|
| JP | A 5-271253 | 10/1993 | |
| JP | A 6-158328 | 6/1994 | |
| JP | A 9-40683 | 2/1997 | |
| JP | A 10-72475 | 3/1998 | |
| JP | A 10-114781 | 5/1998 | |
| JP | A 11-199591 | 7/1999 | |
| JP | A 11-255784 | 9/1999 | |

* cited by examiner

*Primary Examiner*—Porfirio Nazario-Gonzalez
(74) *Attorney, Agent, or Firm*—Young & Thompson

(57) ABSTRACT

A process of producing a strontium titanate, barium titanate or barium strontium titanate thin film by chemical vapor deposition which comprises using a titanium compound represented by formula (I):

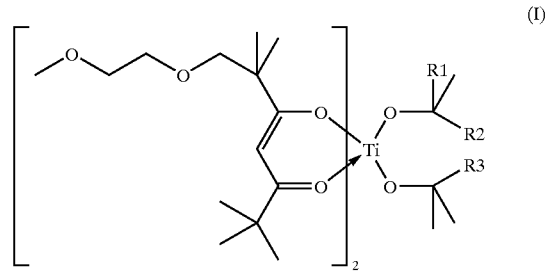

wherein $R^1$ represents a hydrogen atom or a methyl group; and $R^2$ and $R^3$ each represent a methyl group or an ethyl group, or $R^2$ and $R^3$ are connected together to form a methylene group, a methylmethylene group or a dimethyl-methylene group.

2 Claims, 2 Drawing Sheets

PROCESS OF FORMING THIN FILM AND PRECURSOR FOR CHEMICAL VAPOR DEPOSITION

BACKGROUND OF THE INVENTION

1. Field of the Invention

The present invention relates to a process for producing a thin film of strontium titanate (hereinafter referred to as STO), barium titanate (hereinafter referred to as BTO) or barium strontium titanate (hereinafter abbreviated as BST) by chemical vapor deposition (CVD) using a specific titanium compound as a precursor and to a CVD precursor comprising the specific titanium compound.

2. Description of Related Art

Thin films of a titanium-alkaline earth metal composite oxide typified by STO, BTO or BST are expected for application to semiconductors and electronic components because of their unique electrical characteristics, such as high dielectric constants. In particular, their application to semiconductor memories as a capacitor has been under study.

Processes for making a thin film of STO, BTO or BST include CVD, flame hydrolysis deposition, sputtering, ion plating, and metal-organic decomposition (MOD) such as dipping-pyrolysis process and a sol-gel process. Among these thin film forming technologies, CVD is the most suitable process because of ease of composition control, excellent step coverage, suitability to large volume production, and capabilities of hybrid integration, as is reported, e.g., in JP-A-6-158328.

Ti source precursors fit for CVD include titanium tetraalkoxides, e.g., titanium tetraisopropoxide. However, when they are combined with St- and/or Ba-supplying precursors for CVD, it is difficult to establish strategy for stable and industrial production of STO, BTO or BST thin films having ease of composition control and excellent step coverage on account of mismatch between the Ti source precursors and the St and/or Ba source precursors in terms of vaporization characteristics or decomposition behavior.

Ti source precursors for CVD also include titanium complexes having a β-diketone as a ligand. For example, JP-A-5-271253, JP-A-9-40683, JP-A-10-72475, JP-A-10-114781, JP-A-11-199591 and JP-A-11-255784 disclose titanium compounds having an alkyl-terminated β-diketone represented by 2,2,6,6-tetramethylheptane-3,5-dione. These materials are also unsatisfactory for the same reasons as described above. They involve an additional problem that the titanium content in a resulting thin film falls short of what is designed.

SUMMARY OF THE INVENTION

An object of the present invention is to provide a process of forming an STO, BTO or BST thin film by CVD which can be performed stably enough for industrialization and to provide a precursor for CVD.

As a result of extensive investigation, the present inventors have found that the above object is accomplished by a titanium compound having a specific molecular structure and completed the present invention.

The present invention provides a process of producing an STO, BTO or BST thin film by CVD, which comprises using a titanium compound represented by formula (I):

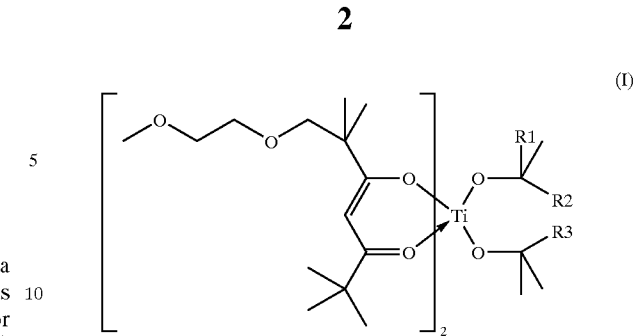

wherein $R^1$ represents a hydrogen atom or a methyl group; and $R^2$ and $R^3$ each represent a methyl group or an ethyl group, or $R^2$ and $R^3$ are connected together to form a methylene group, a methylmethylene group or a dimethylmethylene group.

The present invention further provides a precursor for CVD comprising a titanium compound represented by formula (III):

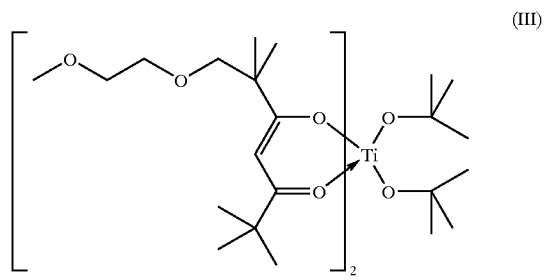

The present invention furthermore provides a precursor for CVD comprising a titanium compound represented by formula (IV):

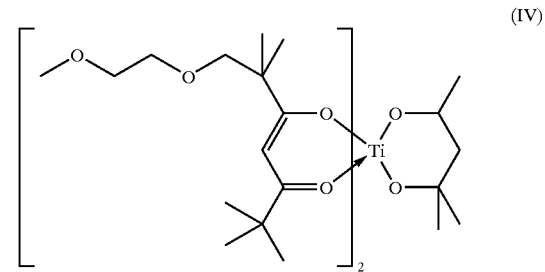

BRIEF DESCRIPTION OF THE DRAWINGS

The present invention will be more particularly described with reference to the accompanying drawings, in which.

DETAILED DESCRIPTION OF THE PREFERRED EMBODIMENTS

Figure 1:
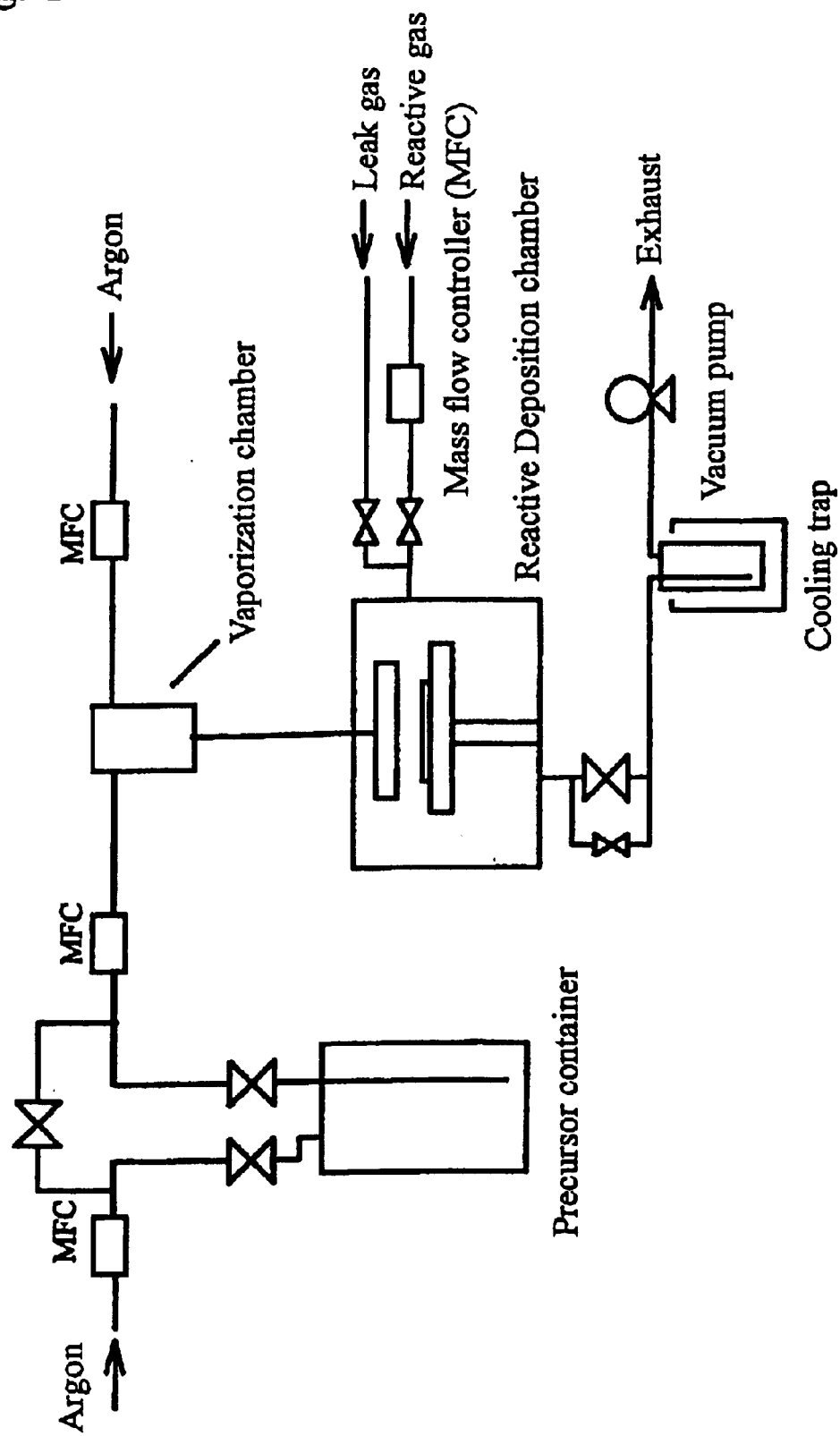
FIG. 1 schematically illustrates a single source CVD apparatus used for thin film formation.

The titanium compound of formula (I), which can be used to form thin films of STO, BTO or BST according to the process of the invention, includes compound Nos. 1 to 6 shown below.

Compound No. 1:

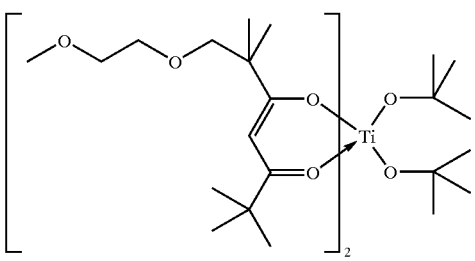

Compound No. 2:

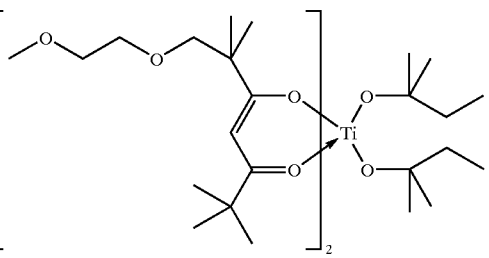

Compound No. 3:

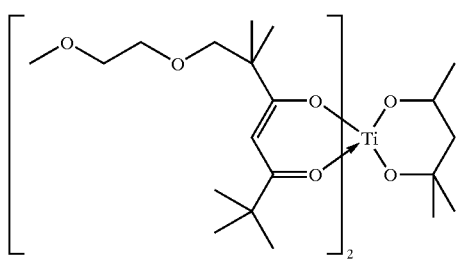

Compound No. 4:

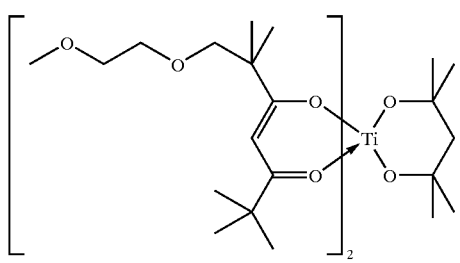

Compound No. 5:

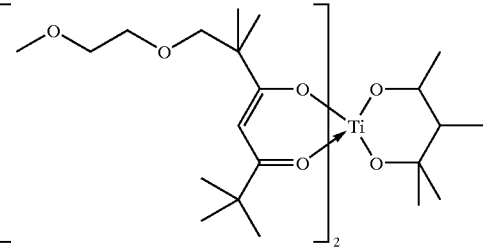

Compound No. 6:

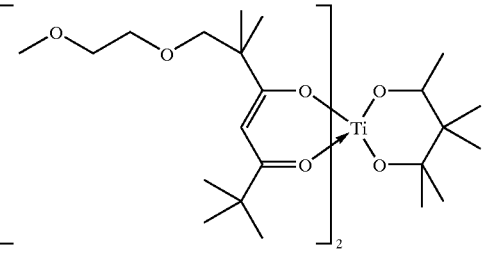

The titanium compound of formula (I) can be prepared by any known process with no particular restriction. For example, it is synthesized by the reaction between titanium tetrachloride and ligand compounds, i.e., a β-diketone compound and an alcohol (or diol) compound, in the presence of a base (e.g., sodium hydroxide or ammonia) or by the ligand exchange reaction between a titanium lower alkoxide (e.g., tetramethoxide, tetraisopropoxide or tetra-t-butoxide) and the ligand compounds.

The ligand exchange reaction technique includes a method in which the ligand exchange between the lower alkoxide and the ligand compounds (i.e., a combination of a β-diketone compound and an alcohol compound or a combination of a β-diketone compound and a diol compound) is carried out all at once, a method in which the ligand exchange between the lower alkoxide and the alcohol or diol compound is followed by the exchange between the resultant intermediate alkoxide and the β-ketone compound, and a method in which the exchange between the lower alkoxide and the β-diketone compound is followed by the exchange between the residual alkoxy group and the alcohol or diol compound.

The strontium compound and the barium compound which can be used in the process of the invention are not at all limited, and any compounds available as a strontium source or a barium source for CVD can be used. In particular, strontium or barium compounds represented by formula (II) shown infra are preferred for their advantages such as stable vaporization capabilities, chemical stability, and organic solvent solubility which favors to liquid delivery hereinafter described.

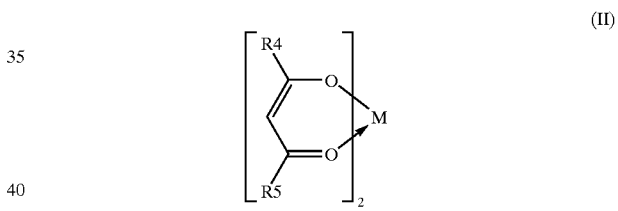

(II)

wherein $R^4$ represents a trifluoromethyl group, a pentafluoroethyl group or an alkyl group having 1 to 8 carbon atoms which may contain an oxygen atom in the carbon chain thereof; $R^5$ represents a trifluoromethyl group, a pentafluoroethyl group or an alkyl group having 1 to 5 carbon atoms; and M represents a strontium atom or a barium atom.

In formula (II) $R^4$, an alkyl group having 1 to 8 carbon atoms which may contain an oxygen atom in the carbon chain thereof, includes methyl, ethyl, propyl, isopropyl, butyl, isobutyl, sec-butyl, t-butyl, amyl, isoamyl, t-amyl, 1-ethylbutyl, 1,1-dimethylpropyl, 1-methylpentyl, 1,1-dimethylbutyl, hexyl, cyclohexyl, heptyl, isoheptyl, t-heptyl, 1-ethylpentyl, 1-methylcyclohexyl, n-octyl, isooctyl, t-octyl, 2-ethylhexyl, methoxymethyl, 1-methoxyethyl, 1-methoxy-1-methylethyl, 2-methoxyethyl, 2-methoxy-1-methylethyl, 2-methoxy-1,1-dimethylethyl, (2-methoxyethoxy)methyl, 1-(2-methoxyethoxy)ethyl, 1-(2-methoxyethoxy)-1-methylethyl, 2-(2-methoxyethoxy)ethyl, 2-(2-methoxyethoxy)-1-methylethyl, and 2-(2-methoxyethoxy)-1,1-dimethylethyl. The alkyl group having 1 to 5 carbon atoms as represented by $R^5$ includes methyl, ethyl, propyl, isopropyl, butyl, isobutyl, sec-butyl, t-butyl, amyl, isoamyl, and t-amyl.

Compound Nos. 7 to 12 shown below are examples of the strontium compound represented by formula (II).

Compound No. 7:
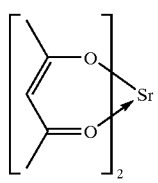
Compound No. 8:
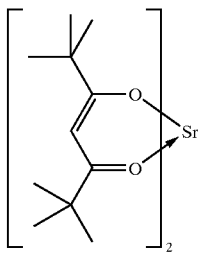
Compound No. 9:
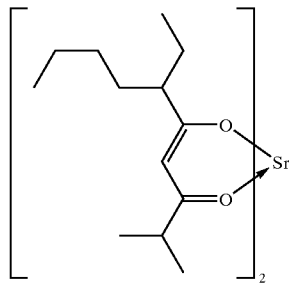
Compound No. 10:
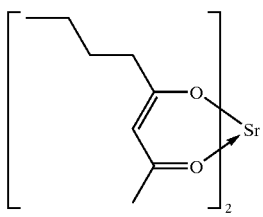
Compound No. 11:
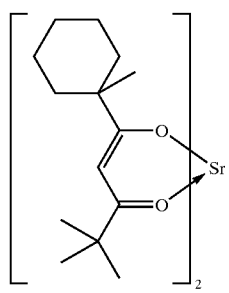
Compound No. 12:
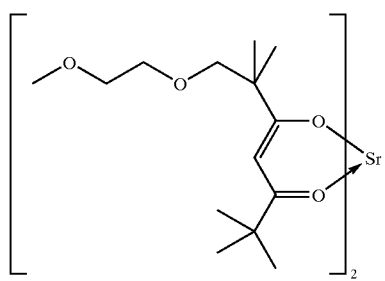
Compound No. 13:
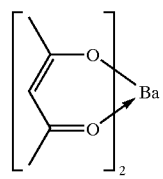
Compound No. 14:
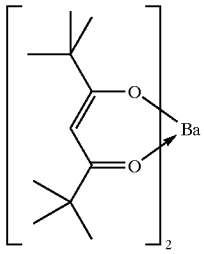
Compound No. 15:
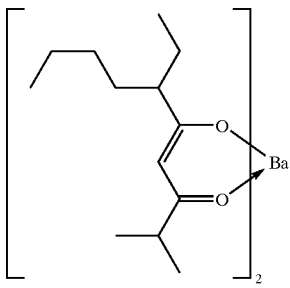
Compound No. 16:
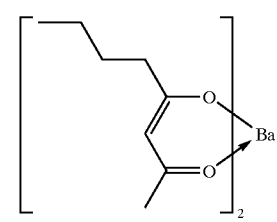
Compound No. 17:
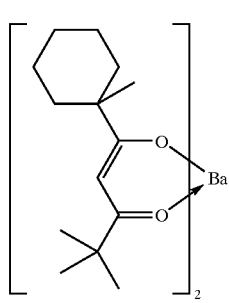
Compound No. 18:
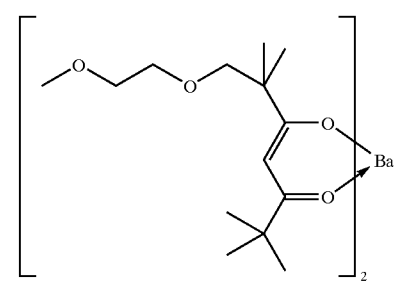
Compound Nos. 13 to 18 shown below are examples of the barium compound represented by formula (II).
Where the strontium or barium compound of formula (II) is used in the CVD, the titanium compound represented by formula (I) which matches the compound of formula (II) in vaporization characteristics or decomposition behavior is the one wherein $R^1$, $R^2$, and $R^3$ are each a methyl group (i.e., compound No. 1 represented by formula (III)) and the one wherein $R^1$ is a hydrogen atom, and $R^2$ and $R^3$ are taken together to form a methylene group (i.e., compound No. 3 represented by formula (IV)).

Accordingly, CVD precursors containing the titanium compound of formula (III) or (IV) are particularly preferred for use in the present invention.

The process of producing an STO, BTO or BST thin film according to the present invention is by a CVD process using the titanium compound of formula (I). A CVD process comprises leading a vaporized precursor and, if necessary, a reactive gas to a substrate and allowing the precursor vapor to decompose and/or react to form a ceramic which is deposited on the substrate. The process of the present invention is not particularly restricted by the method of feeding the precursors, the mode of deposition, the production conditions, the production equipment, and so forth.

The reactive gas which can be used if necessary includes oxygen, ozone, nitrogen dioxide, nitrogen monoxide, and steam.

The methods of feeding the precursors include a gas delivery system and a liquid delivery system. In a gas deliver system the CVD precursor in a container is vaporized by heating and/or vacuum evacuation and led to a deposition reaction site (the surface of a substrate) together with, if desired, a carrier gas, e.g., argon, nitrogen or helium. In a liquid delivery system the CVD precursor in a liquid or solution state is fed to a vaporization chamber, where it is vaporized by heating and/or vacuum evacuation and then led to a deposition reaction site. STO, BTO, and BST being of multi-component system, the methods of feeding precursors are also divided into a multi-source system in which a plurality of monometallic precursors are used and a single source system using a mixed precursor comprising a plurality of precursors at a prescribed ratio.

According to the energy applied to the vaporized precursor or a mixture of the vaporized precursor and a reactive gas, the deposition modes include thermal CVD (only heat energy is used), plasma-enhanced CVD (heat and plasma are used), photo-assisted CVD (heat and light are used), photo plasma-assisted CVD (heat, light and plasma are used), and atomic layer deposition (ALD) (an elementary reaction for forming a monomolecular layer is repeated until a desired thickness is gained).

The production conditions include temperature (the substrate temperature), pressure, and deposition rate. The temperature is preferably 200° C. or higher at which the metallic compounds (CVD precursors) decompose sufficiently, still preferably 350 to 800° C. The pressure is from atmospheric pressure to 10 Pa for thermal CVD and photo-assisted CVD or from 10 to 2000 Pa for plasma-enhanced CVD. The deposition rate can be controlled by the precursor feed conditions (vaporizing temperature, vaporizing pressure, solution feed rate, etc.) and the reaction temperature and pressure. Too high a deposition rate tends to result in deteriorated electrical characteristics of the thin film, such as a specific dielectric constant and a leakage current, and too low a deposition rate tends to result in poor productivity. A preferred deposition rate ranges 0.1 to 1000 nm/min, particularly 1 to 500 um/min.

In the process of the present invention, the resulting STO, BTO or BST thin film may be subjected to annealing to obtain improved electrical characteristics. Where step coverage is required, the process can have the step of reflowing the thin film at 600 to 1200° C., preferably 700 to 1000° C.

The term "precursor for CVD (or CVD precursor)" as referred to in the present invention is the titanium compound of formula (I) itself in gas delivery system CVD, or the liquid titanium compound or a solution of the titanium compound in an organic solvent in liquid delivery system CVD. In a single source CVD, a mixture comprising the titanium compound and at least one of a strontium compound and, a barium compound or a solution of the mixture is the CVD precursor.

The organic solvent which is used in liquid CVD precursors is not particularly limited and any well-known organic solvent is useful. Examples are alcohols, such as methanol, ethanol, 2-propanol, and n-butanol; acetic esters, such as ethyl acetate, butyl acetate, and methoxyethyl acetate; ether alcohols, such as ethylene glycol monomethyl ether, ethylene glycol monoethyl ether, ethylene glycol monobutyl ether, and diethylene glycol monomethyl ether; ethers, such as tetrahydrofuran, ethylene glycol dimethyl ether, diethylene glycol dimethyl ether, triethylene glycol dimethyl ether, and dibutyl ether; ketones, such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons, such as hexane, cyclohexane, methylcyclohexane, ethylcyclohexane, heptane, octane, toluene, and xylene; hydrocarbons having a cyano group, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; pyridine, and lutidine. A solvent to be used should be properly chosen according to, for example, solubility for the solute and the boiling temperature or ignition temperature in relation to the working temperature.

The concentration of the CVD precursor solution is not particularly limited as long as the solution can be supplied stably, and an appropriate concentration is decided according to the desired amount of the precursor to be delivered, the film growth rate, and the like. Concentrations lower than 0.05 mol/l tend to result in small film growth rates due to reduced metal source feed. Concentrations higher than 0.5 mol/l tend to result in poor flowability of the precursor solution or such unfavorable phenomena as precipitation. Accordingly, a preferred concentration is in the range of from 0.05 to 0.5 mol/l.

If desired, the CVD precursor according to the present invention can contain a nucleophilic reagent to stabilize the metal compound. Examples of suitable nucleophilic reagents include ethylene glycol ethers, such as glyme, diglyme, triglyme, and tetraglyme; crown ethers, such as 18-crown-6, dicyclohexyl-18-crown-6, 24-crown-8, dicyclohexyl-24-crown-8, and dibenzo-24-crown-8; polyamines, such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, and 1,1,4,7,10,10-hexamethyl-triethylenetetramine; cyclic polyamines, such as cyclam and cyclen; β-ketonic esters or β-diketones, such as methyl acetoacetate, ethyl acetoacetate, and 2-methoxyethyl acetoacetate. The nucleophilic reagent as a stabilizer is used in an amount of 0.1 to 10 mol, preferably 1 to 4 mol, per mole of the metal compound.

The present invention will now be illustrated in greater detail with reference to Examples and Comparative Examples, but it should be understood that the present invention is not construed as being limited thereto.

PREPARATION EXAMPLE 1

Synthesis of Compound No. 1:

Into a 500 ml reactive flask purged with argon were put 100 ml of dried hexane, 0.332 mol of titanium tetra-t-butoxide, and 0.664 mol of 1-(2-methoxyethoxy)-2,2,6,6-tetramethyl-3,5-heptanedione, and the mixture was stirred at 45° C. for 2 hours. The solvent and other low-boiling components were removed by evaporation, and the residue was purified by vacuum distillation (column top temperature: 185–188° C., 0.2 Torr) to give a product in a yield of 68.1%, which was identified to be compound No. 1 by $^1$H-NMR and elemental analyses. The purity of the compound was confirmed by HPLC.

$^1$H-NMR: (1.11–1.60; m; 48H), (3.13; s; 3H), (3.16; s; 3H), (3.17–3.67; m+m+m; 12H), (5.92; s; 2H)

Elemental analysis (wt %): Calcd.: C 61.00; H 9.67; Ti 6.76. Found: C 61.0; H 9.65; Ti 6.77.

HPLC (solvent: tetrahydofuran (THF); column: GPC; flow rate: 0.5 ml/min; retention time: 15.12 min):

Purity: 100%

PREPARATION EXAMPLE 2

Synthesis of Compound No. 3:

Into a 500 ml reactive flask purged with argon were put 100 ml of dried xylene, 0.332 mol of titanium tetraisopropoxide, and 0.664 mol of 1-(2-methoxyethoxy)-2,2,6,6-tetramethyl-3,5-heptanedione, and the mixture was refluxed at 60° C. for 2 hours. To the reaction mixture was added 0.4 mol of 2-methyl-2,4-pentanediol, followed by stirring at 140° C. for 3 hours. The solvent and other low-boiling components were evaporated, and the residue was purified by vacuum distillation (column top temperature: 190–193° C.; 0.3–0.4 Torr) to give a product in a yield of 90.6%, which was identified to be compound No. 3 by $^1$H-NMR and elemental analyses. The purity of the compound was confirmed by HPLC.

$^1$H-NMR: (0.89–1.58; m; 39H), (1.81–1.86; d; 1H), (1.96–2.00; m; 1H), (3.15; s; 6H), (3.32; s; 4H), (3.52; s; 8H), (4.94–5.21; br; 1H), (6.01; s; 2H)

Elemental analysis (wt %): Calcd.: C 60.16; H 9.21; Ti 7.06. Found: C 60.2; H 9.20; Ti 7.08.

HPLC (solvent: THF; column: GPC; flow rate: 0.5 ml/min; retention time: 17.07 min):

Purity: 100%

Characterization of Titanium Compounds:

Each of compound Nos. 1 and 3 and comparative compounds A to D shown infra was analyzed on a differential calorimeter in a dried argon stream (100 ml/min) at a rate of temperature rise of 10° C./min. The residual amount at 400° C. and the 50% weight loss temperature were measured, and the 50% weight loss temperature was compared with that of compound No. 8 (strontium compound) and compound No. 14 (barium compound). The results of measurement and comparison are shown in Table 1 below. For a compound to have a residue at 400° C. in the analysis means to undergo pyrolysis before or during vaporization. The smaller the residue amount, the fitter the compound as a CVD precursor. A compound of which the 50% weight loss temperature is closer to that of the strontium compound and/or the barium compound matches more with the strontium compound and/or the barium compound in vaporization characteristics and is more suited to single source CVD, in which a plurality of CVD precursors are vaporized simultaneously.

Comparative Compound A:

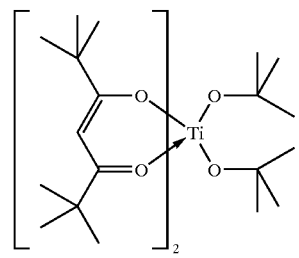

Comparative Compound B:

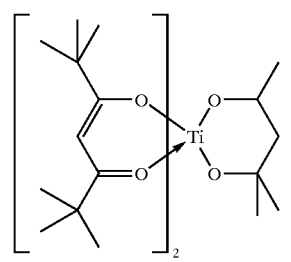

Comparative Compound C:

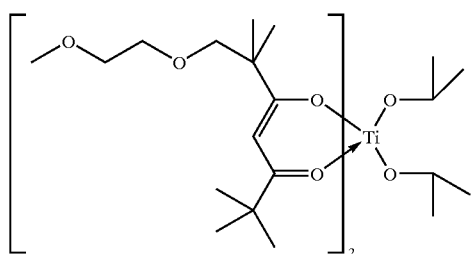

Comparative Compound D:

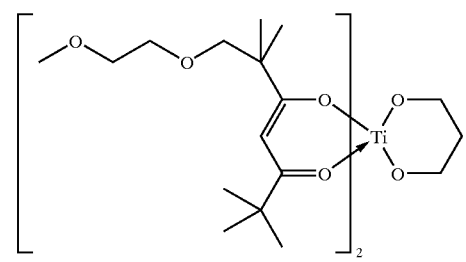

TABLE 1

| Ti Compound | 400° C. Residue (%) | 50% Weight Loss Temperature (° C.) | Δ50% Weight Loss Temp. w.r.t. Compound No. 8* (° C.) | Δ50% Weight Loss Temp. w.r.t. Compound No. 14** (° C.) |
|---|---|---|---|---|
| No. 1 | 0 | 303 | −47 | −54 |
| No. 3 | 0 | 307 | −43 | −50 |
| A | 0 | 255 | −95 | −102 |
| B | 0 | 242 | −108 | −115 |
| C | 8.1 | 280 | −70 | −77 |
| D | 6.2 | 289 | −61 | −68 |

*50% Weight loss temp. of compound No. 8: 350° C.
**50% Weight loss temp. of compound No. 14: 357° C.

EXAMPLE 1

An STO thin film was formed on a silicon wafer (substrate) by means of a CVD apparatus shown in FIG. 1 using, as a single source precursor, a solution of 0.05 mol of compound No. 3 and 0.05 mol of compound No. 8 in 1000 ml of THF (water content: ≦1 ppm) under the following conditions.

Vaporization chamber temperature: 260° C.
Precursor feed rate: 0.10 ml/min
Oxygen gas feed rate: 420 sccm
Reaction pressure: 700–1200 Pa
Reaction time: 15 mins
Substrate temperature: 600° C.

The thin film thus formed was analyzed by X-ray diffractometry to confirm the peak of STO. The composition of the thin film was investigated by ICP elemental analysis on the film separated from the substrate by soaking in a 5% hydrofluoric acid aqueous solution. As a result, the X-ray diffraction pattern showed an STO peak at 2 θ=33°, and the ICP elemental analysis revealed that the Sr/Ti molar ratio of the film was 1.00/0.95.

COMPARATIVE EXAMPLE 1

An STO thin film was formed in the same manner as in Example 1, except for replacing compound No. 3 as a titanium compound with comparative compound A. The film was analyzed in the same manner as in Example 1. As a result, the X-ray diffraction pattern showed an STO peak at 2 θ=33°, and the Sr/Ti molar ratio of the film was found to be 1.00/0.79.

COMPARATIVE EXAMPLE 2

An STO thin film was formed in the same manner as in Example 1, except for replacing compound No. 3 as a titanium compound with comparative compound B. The film was analyzed in the same manner as in Example 1. As a result, the X-ray diffraction pattern showed an STO peak at 2 θ=33°, and the Sr/Ti molar ratio of the film was found to be 1.00/0.72.

EXAMPLE 2

An STO thin film was formed in the same manner as in Example 1, except for using, as a single source precursor, a solution of 0.075 mol of compound No. 3 and 0.075 mol of compound No. 12 in 1000 ml of diglyme (water content: <1 ppm) under the following conditions.

Vaporization chamber temperature: 280° C.
Precursor feed rate: 0.10 ml/min
Oxygen gas flow rate: 420 sccm
Reaction pressure: 700–1200 Pa
Reaction time: 10 mins
Substrate temperature: 600° C.

The film was analyzed in the same manner as in Example 1. As a result, the X-ray diffraction pattern showed an STO peak at 2 θ=33°, and the Sr/Ti molar ratio of the film was found to be 1.00/0.97.

COMPARATIVE EXAMPLE 3

An STO thin film was formed in the same manner as in Example 2, except for replacing compound No. 3 as a titanium compound with comparative compound A. The film was analyzed in the same manner as in Example 1. As a result, the X-ray diffraction pattern showed an STO peak at 2 θ=33°, and the Sr/Ti molar ratio of the film was found to be 1.00/0.78.

COMPARATIVE EXAMPLE 4

An STO thin film was formed in the same manner as in Example 2, except for replacing compound No. 3 as a titanium compound with comparative compound B. The film was analyzed in the same manner as in Example 1. As a result, the X-ray diffraction pattern showed an STO peak at 2 θ=33°, and the Sr/Ti molar ratio of the film was found to be 1.00/0.80.

EXAMPLE 3

Figure 2:
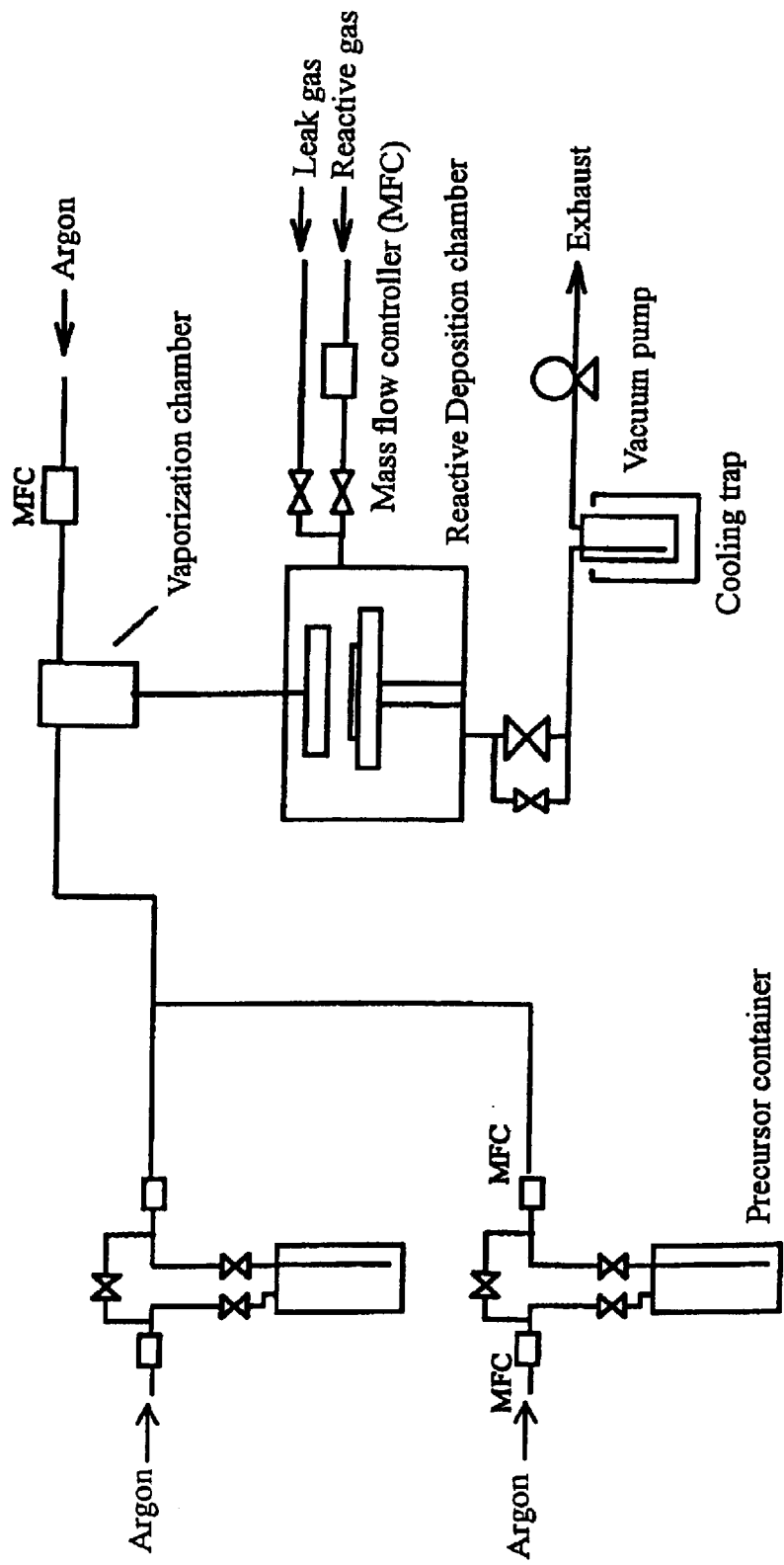
FIG. 2 schematically illustrates a multi-source CVD apparatus used for thin film formation.

An STO thin film was formed on a silicon wafer (substrate) by means of a CVD apparatus shown in FIG. 2 using, as a multi-source precursor, a solution of 0.05 mol of compound No. 1 in 1000 ml of THF (water content: ≦1 ppm) as a Ti source and a solution of 0.05 mol of compound No. 8 in 1000 ml of THF (water content: ≦1 ppm) as an Sr source under the following conditions.

Vaporization chamber temperature: 260° C.
Precursor feed rate: 0.080 ml/min each
Oxygen gas feed rate: 475 sccm
Reaction pressure: 700–1200 Pa
Reaction time: 10 mins
Substrate temperature: 600° C.

The thin film thus formed was analyzed by X-ray diffractometry to confirm the peak of STO. The composition of the thin film was investigated by ICP elemental analysis on the film separated from the substrate by soaking in a 5% hydrofluoric acid aqueous solution. As a result, the X-ray diffraction pattern showed an STO peak at 2 θ=33°, and the ICP elemental analysis revealed that the Sr/Ti molar ratio of the film was 1.00/0.97.

EXAMPLE 4

A BST thin film was formed on a silicon wafer (substrate) by means of a CVD apparatus shown in FIG. 1 using, as a single source precursor, a solution of 0.05 mol of compound No. 1, 0.015 mol of compound No. 8, and 0.035 mol of compound No. 14 in 1000 ml of THF (water content: ≦1 ppm) under the following conditions.

Vaporization chamber temperature: 260° C.
Precursor feed rate: 0.08 ml/min
Oxygen gas feed rate: 470 sccm
Reaction pressure: 700–1200 Pa
Reaction time: 15 mins
Substrate temperature: 600° C.

The thin film thus formed was analyzed by X-ray diffractometry to confirm the peaks of BST. The composition of the thin film was investigated by ICP elemental analysis on the film separated from the substrate by soaking in a 5% hydrofluoric acid aqueous solution. As a result, the X-ray diffraction pattern showed BST peaks at 2 θ=32°, 47°, and 57°, and the ICP elemental analysis revealed that the Ba/Sr/Ti molar ratio of the film was 0.35/0.14/0.49.

EXAMPLE 5

A BST thin film was formed on a silicon wafer (substrate) by means of a CVD apparatus shown in FIG. 1 using, as a single source precursor, a solution of 0.07 mol of compound No. 3, 0.04 mol of compound No. 12, and 0.03 mol of compound No. 18 in 1000 ml of diglyme (water content: ≦1 ppm) under the following conditions.

Vaporization chamber temperature: 280° C.
Precursor feed rate: 0.10 ml/min
Oxygen gas feed rate: 470 sccm
Reaction pressure: 700–1200 Pa
Reaction time: 10 mins
Substrate temperature: 600° C.

The thin film thus formed was analyzed by X-ray diffractometry to confirm the peak of BST. The composition of the thin film was investigated by ICP elemental analysis on the film separated from the substrate by soaking in a 5% hydrofluoric acid aqueous solution. As a result, the X-ray diffraction pattern showed BST peaks at 2 θ=32°, 47°, and 57°, and the Ba/Sr/Ti molar ratio of the film was found to be 0.29/0.40/0.71.

The present invention provides a process of stably producing an STO, BTO or BST thin film by CVD which can be applied to industrialization and a precursor for establishing the process.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

This application claims the priority of Japanese Patent Application No. 2001-350691 filed Nov. 15, 2001, which is incorporated herein by reference.

What is claimed is:

1. A precursor for chemical vapor deposition comprising a titanium compound represented by formula (III):

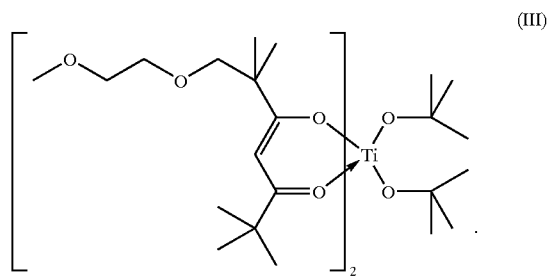

2. A precursor for chemical vapor deposition comprising a titanium compound represented by formula (IV):

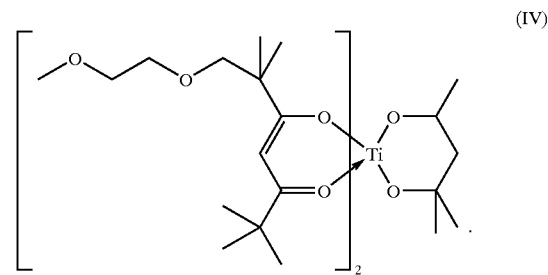

* * * * *